United States Patent [19]
Schroeppel et al.

[11] Patent Number: 5,908,447
[45] Date of Patent: Jun. 1, 1999

[54] BREAKAWAY STRUCTURE FOR BODY IMPLANTABLE MEDICAL DEVICE

[75] Inventors: Edward A. Schroeppel; James E. Machek; Paul R. Spehr, all of Lake Jackson, Tex.

[73] Assignee: Intermedics Inc., Angleton, Tex.

[21] Appl. No.: 09/020,184

[22] Filed: Feb. 6, 1998

[51] Int. Cl.$^6$ .......................................................... A61N 1/06

[52] U.S. Cl. .......................................................... 607/126

[58] Field of Search ................................... 607/122, 126, 607/128

[56] References Cited

U.S. PATENT DOCUMENTS

| | | | |
|---|---|---|---|
| 3,835,864 | 9/1974 | Rasor et al. | 128/419 P |
| 4,258,724 | 3/1981 | Balat et al. | 607/128 |
| 4,516,584 | 5/1985 | Garcia | 128/785 |
| 4,820,298 | 4/1989 | Leveen et al. | 623/1 |
| 4,883,070 | 11/1989 | Hawson | 607/122 |
| 4,950,258 | 8/1990 | Kawai et al. | 604/281 |
| 5,049,591 | 9/1991 | Hayashi et al. | 521/159 |
| 5,108,417 | 4/1992 | Sawyer | 606/198 |
| 5,128,197 | 7/1992 | Kobayashi et al. | 428/225 |
| 5,129,404 | 7/1992 | Spehr et al. | 128/785 |
| 5,129,405 | 7/1992 | Milijasevic et al. | 128/785 |
| 5,189,110 | 2/1993 | Ikematu et al. | 525/314 |
| 5,273,053 | 12/1993 | Pohndorf | 607/132 |
| 5,545,204 | 8/1996 | Cammilli et al. | 607/123 |
| 5,575,766 | 11/1996 | Swartz et al. | 604/53 |
| 5,617,854 | 4/1997 | Munsif | 128/642 |
| 5,632,734 | 5/1997 | Galel et al. | 604/282 |
| 5,634,936 | 6/1997 | Linden et al. | 606/123 |

FOREIGN PATENT DOCUMENTS

| | | | |
|---|---|---|---|
| WO93/06792 | 4/1993 | WIPO | A61F 2/06 |

OTHER PUBLICATIONS

C. Liang et al., *Preliminary Investigation of Shape Memory Polymers and Their Hybrid Composites*, Smart Structures and Materials ASME, AD–vol. 24/AMD–Vol. 123, pp. 97–105, 1991.

Paul Frenger, *Biomedical Uses of Shape Memory Polymers*, Biomedical Sciences Instrumentation, vol. 29, pp. 47–50, 1993.

N. Koczera et al., *Shape Memory Polymers For Surgical Staples*, Proceedings of the 12$^{th}$ Southern Biomedical Engineering Conference in New Orleans, IEEE, pp. 60–62, 1993.

Manas Chanda et al., *Plastics Technology Handbook*, Plastics Technology Handbook, Chapter 6, pp. 721–723, 1993.

S. Hayashi et al., *Properties and Applications of Polyurethane–Series Shape Memory Polymer*, ANTEC '94, pp. 1998–2001, 1994.

(List continued on next page.)

*Primary Examiner*—William Kamm
*Attorney, Agent, or Firm*—John R. Merkling; Trop, Pruner, Hu & Miles, P.C.

[57] ABSTRACT

A cardiac lead is provided that includes a connector for connecting to a cardiac stimulator and a flexible sleeve coupled to the connector. The sleeve has a first segment, a second segment and a jacket coupling the first segment and the second segment. The jacket is composed of a shape-memory polymeric material which deforms diametrically in situ to selectively disconnect the first segment from the second segment. An electrode is coupled to the sleeve and a conductor is disposed in the sleeve and coupled to the connector and the electrode for conveying electrical signals. The breakaway function of the jacket allows removal of all but a small portion of the lead without dissection of fibrous tissue.

4 Claims, 7 Drawing Sheets

OTHER PUBLICATIONS

V. Tucci et al., *Shape Memory Polymers For External Fracture Fixation*, ANTEC '95, pp. 2102–2104, 1995.

Shunichi Hayashi et al., *Room–Temperature–Functional Shape–Memory Polymers*, Plastics Engineering, pp. 29–31, Feb. '95.

C. Daubert et al., *Permanent Left Atrial Pacing with a Specifically Designed Coronary Sinus Lead*, PACE, vol. 18, p. 1180, May 1995.

Robert R. Brownlee et al., *Toward Optimizing a Preshaped Catheter and System Parameters to Acheive Single Lead DDD Pacing*, PACE, vol. 20, pp. 1354–1358, May 1997.

S. Echigo et al., *Development of a New Transvenous Patent Ductus Arteriosus Occlusion Technique Using a Shape Memory Polymer*, ASAIO Transactions, vol. 36, n. 3, pp. M195–M198, Jul. 1990.

Francis D. Murgatroyd et al., *Atrial Fibrillation: The Last Challenge in International Electrophysiology*, British Heart Journal, vol. 74 #3, pp. 209–211, 1995.

BREAKAWAY STRUCTURE FOR BODY IMPLANTABLE MEDICAL DEVICE

BACKGROUND OF THE INVENTION

1. Field of the Invention

This invention relates generally to cardiac stimulator leads, and more particularly to a cardiac lead having a shape-memory polymeric breakaway structure, such as a passive fixation tine or the distal end of a lead sleeve.

2. Description of the Related Art

Conventional cardiac stimulator systems consist of a cardiac stimulator and an elongated flexible cardiac lead that is connected proximally to a header structure on the cardiac stimulator and is implanted distally at one or more sites within the heart requiring cardiac stimulation or sensing. The cardiac stimulator is normally a pacemaker, a cardioverter/defibrillator, a sensing instrument, or some combination of these devices.

At the time of implantation, the distal end of a cardiac lead is inserted through an incision in the chest and manipulated by the physician to the site requiring electrical stimulation with the aid of a flexible stylet that is removed prior to closure. At the site requiring electrical stimulation, the distal end of the lead is anchored to the endocardium by an active mechanism, such as a screw-in electrode tip or, alternatively, by a passive mechanism, such as one or more radially spaced tines that engage the endocardium. The proximal end of the lead is then connected to the cardiac stimulator and the incision is closed.

One of the body's normal physiological responses to the engagement of a lead with the endocardium is the production of fibrous tissue around the distal end of the lead. The production of fibrous tissue begins almost immediately after the lead is fixed to the heart and may continue as long as the lead is in place. The extent of fibrous tissue growth varies from patient to patient. In most patients, the tissue envelops several millimeters of the distal end of the lead. However, depending upon the patient's particular physiology, as well as the duration of implantation, the extent of fibrous tissue developed may be much more substantial.

For many endocardial leads, fibrous tissue serves the vital function of providing a relatively permanent anchor for the distal end of the lead. Indeed, screw-in tips and tines are designed to hold the lead in contact with the endocardium until fibrous tissue develops and takes over the job of anchoring the lead in position.

It is not uncommon for recipients of cardiac stimulator systems to require replacement of their existing cardiac leads. There are a variety of medical indications that may prompt lead replacement. Some examples include deterioration of the patient's arrhythmia condition due to disease or injury, new sites of electrical dysfunction within the heart, and lead failure. Where lead replacement is indicated, the physician may choose to remove the existing lead or leave the existing lead in place and implant and connect a new lead to the cardiac stimulator.

The initial step in a normal lead removal procedure involves gently tugging proximally on the proximal end of the lead in an attempt to dislodge the distal end of the lead from the endocardium. Since it is normally desirable to remove the lead intact, care must be taken during this operation to avoid applying excessive thrust to the lead that might otherwise break the lead into sections or disconnect the insulating sleeve of the lead from the electrode structures. If the lead is unintentionally broken during the removal process, the physician may have difficulty successfully removing all of the lead components via the original tissue pathway used to implant the lead. In such circumstances, it may be necessary to insert a femoral catheter and enter the heart through the inferior vena cava in an attempt to fish out the remaining components of the lead. The removal process may be hampered by the presence of the fibrous tissue gripping the lead.

In circumstances where tissue ingrowth is substantial enough to prevent ready removal of the lead, physicians sometimes resort to the introduction of a fibrous tissue cutting tool, which consists of a tubular introducer that is passed over the lead body to the site of tissue ingrowth. The tip of the introducer includes a cutting implement, such as a serrated blade or a laser fiber optic element that is used to cut through the fibrous tissue. Extreme care must be exercised when using this type of fibrous tissue cutting instrument to avoid perforating the walls of the heart. Even with careful administration, some fibrous tissue may be so substantial that cutting may not be successful.

Although a decision to leave an existing lead in place avoids some of the difficulties associated with lead removal, there are, nevertheless, trade-offs associated with such a course of treatment. In circumstances where an existing lead is left in place and a new lead is implanted and connected to the cardiac stimulator, the heart must accommodate an additional tubular structure. Where the existing lead is in the right ventricle, the result is another structure interacting with the patient's tricuspid valve. For some patients, the problem may be compound. There are examples of arrhythmia patients undergoing six such lead replacement procedures whose hearts contain six or more disconnected cardiac leads.

Infection represents another potential problem associated with leaving an existing lead in place following replacement with a new lead. A disconnected cardiac lead may present a pathway for infections originating outside of the heart to bypass the protective function of the pericardial sac and attack the heart from within. This problem seems to arise more frequently in geriatric patients who experience infection in their subcutaneous tissue pockets as a result of the gradual thinning of the dermal layers adjacent to their cardiac stimulators. An infection originating in the subcutaneous pocket of a patient may quickly travel through the lumen of a disconnected lead and attack the myocardium.

The present invention is directed to overcoming or reducing one or more of the foregoing disadvantages.

SUMMARY OF THE INVENTION

In accordance with one aspect of the present invention, a cardiac lead is provided. The cardiac lead includes a connector for connecting to a cardiac stimulator and a flexible sleeve coupled to the connector. The sleeve has a lumen, a first segment and a second segment. The first and second segments are coupled. The second segment is composed of a shape-memory polymeric material which deforms diametrically in situ to selectively disconnect the first segment from the second segment. An electrode is coupled to the sleeve and a conductor is disposed in the sleeve and coupled to the connector and the electrode for conveying electrical signals.

In accordance with another aspect of the present invention, a cardiac lead is provided. The cardiac lead includes a connector for connecting to a cardiac stimulator and a flexible sleeve coupled to the connector. The sleeve has a first segment, a second segment and a jacket coupling the first segment and the second segment. The jacket is composed of a shape-memory polymeric material which deforms diametrically in situ to selectively disconnect the first segment from the second segment. An electrode is coupled to the sleeve and a conductor is disposed in the sleeve and coupled to the connector and the electrode for conveying electrical signals.

In accordance with still another aspect of the present invention, a cardiac lead is provided. The cardiac lead includes a connector for coupling to a cardiac stimulator and a flexible sleeve coupled to the connector that has a first lumen. A clamp is coupled to the flexible tubular sleeve and is composed of a shape-memory polymeric material. A tine is coupled to the clamp and has an end projecting away from the flexible sleeve whereby the clamp may be selectively deformed diametrically in situ to disconnect the tine from the clamp. An electrode is coupled to the sleeve and a conductor wire is coupled to the connector and to the electrode for conveying electrical signals.

In accordance with another aspect of the present invention, an introducer assembly for manipulating a medical device in vivo is provided. The introducer assembly includes a pin adapted to be coupled to the medical device and a tubular introducer coupled to the pin. The introducer is composed of a shape-memory polymeric material which deforms in situ to disconnect the introducer from the pin.

In accordance with still another aspect of the present invention, an introducer assembly for manipulating a medical device in vivo is provided. The introducer assembly includes a tubular introducer and a pin coupled to the introducer and adapted to be coupled to the medical device. The pin is composed of a shape-memory polymeric material which deforms in situ to disconnect the introducer from the pin.

BRIEF DESCRIPTION OF THE DRAWINGS

The foregoing and other advantages of the invention will become apparent upon reading the following detailed description and upon reference to the drawings in which.

DETAILED DESCRIPTION OF SPECIFIC EMBODIMENTS

Figure 1:
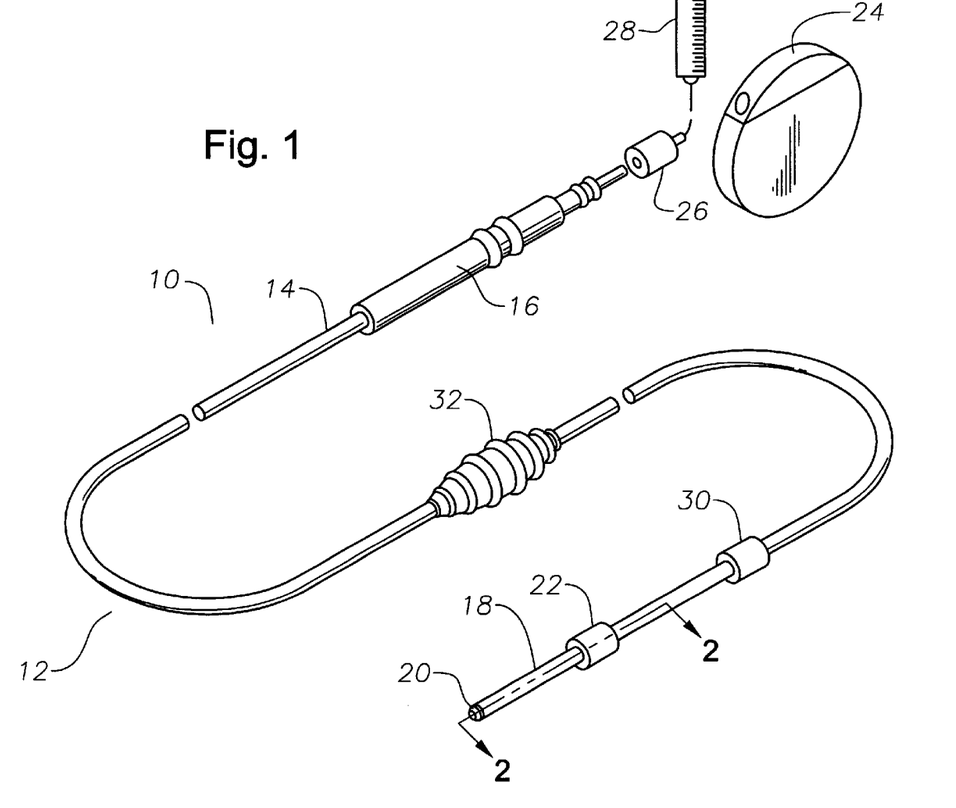
FIG. 1 is a pictorial view of an exemplary embodiment of a cardiac lead and a cardiac stimulator in accordance with the present invention.

In the drawings described below, reference numerals are generally repeated where identical elements appear in more than one figure. Turning now to the drawings, and in particular to FIG. 1, there is shown an exemplary cardiac lead 10 that includes a flexible insulating sleeve 12 that has a proximal segment 14 coupled proximally to a connector 16, and distal segment 18 terminating distally in a tip electrode 20. The proximal and distal segments 14 and 18 are coupled together by a jacket 22. The connector 16 is designed to be inserted into a cardiac stimulator 24, and is shown highly exaggerated in size relative to the cardiac stimulator 24. The cardiac stimulator 24 may be a pacemaker, a cardioverter/defibrillator, or other type of stimulator or a sensing instrument. An adaptor 26 is provided that may be coupled to the connector 16. The adaptor 26 is designed to enable a syringe 28 to be coupled to the connector 16 so that heating or cooling fluid may be injected into the lead 10 as described more below. The illustrated embodiment of the lead 10 is bipolar. Accordingly, the distal end of the segment 14 is provided with an electrode 30 located proximal to the tip electrode 20. However, unipolar arrangements are possible as well. A suture sleeve 32 is slipped over the sleeve 12. During implantation, the suture sleeve 32 is sewn to the vascular wall at the site of transvenous entry.

Figure 2:
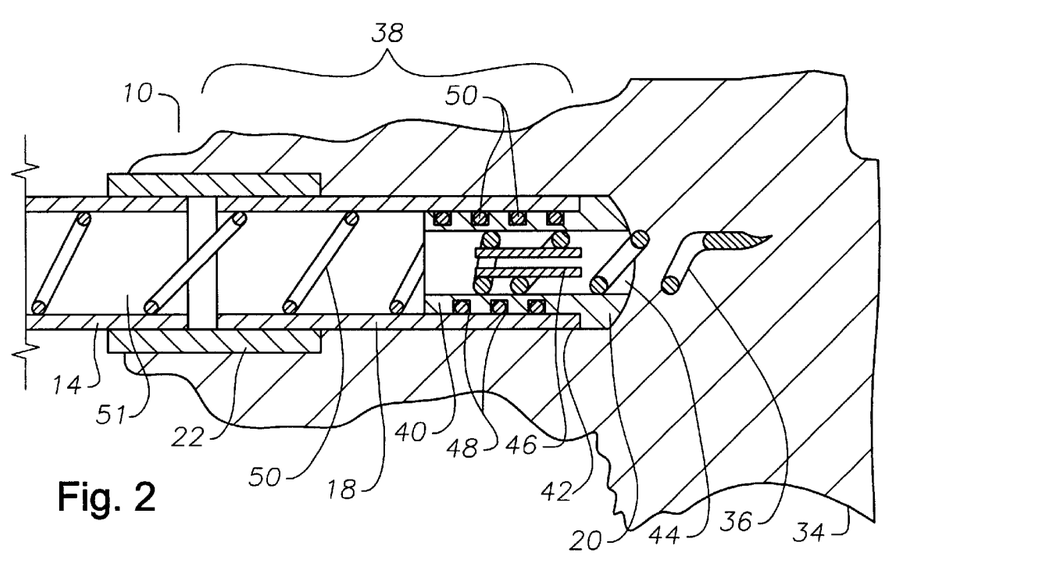
FIG. 2 is a sectional view of the cardiac lead of FIG. 1 taken at section 2—2 in accordance with the present invention.

The detailed structure of the segment 18, the jacket 22 and the union of the segments 18 and 14 may be understood by referring now to FIG. 2, which is a cross-sectional view of FIG. 1 taken at section 2—2. FIG. 2 depicts the lead 10 implanted endocardially and secured to endocardial tissue 34 by a helical screw 36. To better illustrate the present invention, FIG. 2 depicts the lead 10 post-implant and after development of fibrous tissue, designated generally at 38. The fibrous tissue 38 has engulfed the segment 18 and a portion of the jacket 22. The shape and extent of the fibrous tissue 38 shown in FIG. 2 is illustrative as the actual size and shape of fibrous tissue in a given patient will depend on a number of factors, such as the patient's physiology and the period of time following implantation.

The segment 18 is a tubular structure slipped over the proximal end 40 of the tip electrode 20. The proximal end 40 has a smaller outer diameter than the segment 18 so that the distal end of the segment 18 abuts an annular shoulder 42 of the tip electrode 20. The segment 18 is secured to the tip electrode 20 by a suitable medical grade adhesive, such as silicone adhesive. The segment 18 may be composed of a suitable biocompatible polymeric material, such as silicone, polyurethane, or like materials.

The tip electrode 20 has a lumen 44 extending therethrough to enable the passage of fluid introduced by the syringe 28. The helical screw 36 projects distally from the lumen 44 and is connected proximally to the tip electrode 20 via a cylindrical crimp tube 46 that is disposed inside the lumen 44. The helical screw 36 is wrapped around the exterior of the crimp tube 46, and the proximal end 40 of the tip electrode 20 is swaged to secure the helical screw 36 in place. The tip electrode 20, the electrode 30, and the helical screw 36 may be fabricated from a variety of biocompatible conducting materials, such as titanium, stainless steel, iridium oxide coated titanium, or other suitable materials.

The proximal end 40 of the tip electrode 20 is provided with a set of external grooves 48 that are configured much like the external threads of a typical bolt or machine screw. The distal end of a conductor wire 50 is spiraled around the proximal end 40 and disposed in the grooves 48. The conductor wire 50 is connected proximally to the connector 16 shown in FIG. 1. The conductor wire 50 is depicted as a single individually insulated wire with insulation removed from a portion of the wire 50 that is disposed in the grooves 48 so that electrical contact is established between the wire 50 and the tip electrode 20. However, the person of ordinary skill in the art will appreciate that the conductor wire 50 may not be individually insulated if the lead 10 is unipolar or if the various conductor wires in the lead 10 are coaxially arranged or arranged in a nested configuration. Another conductor wire (not shown) couples the electrode 30 shown in FIG. 1 to the connector 16.

Figure 3:
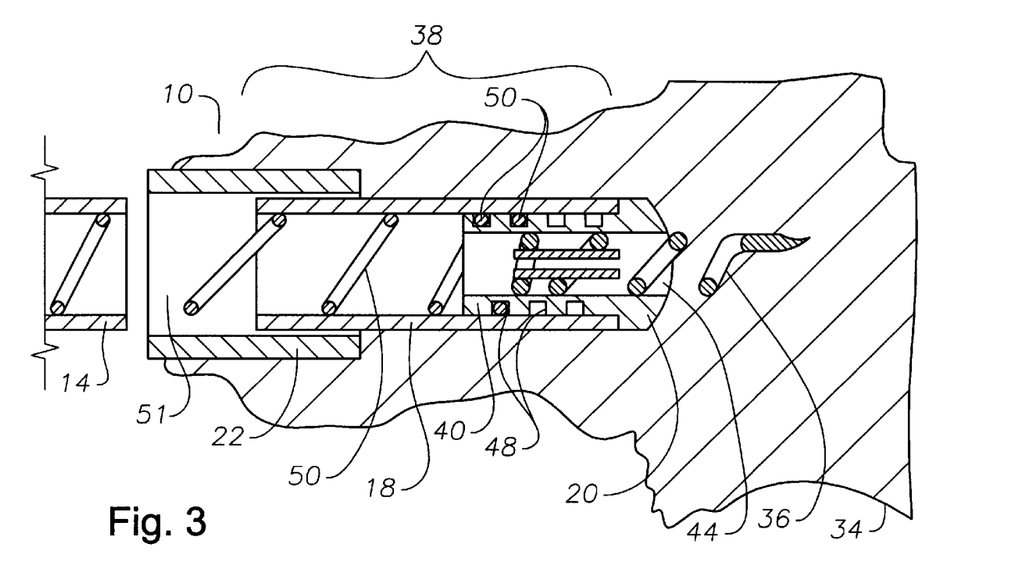
FIG. 3 is a cross-sectional view like FIG. 2 depicting disconnection and withdrawal of a segment of the lead in accordance with the present invention.
Figure 4:
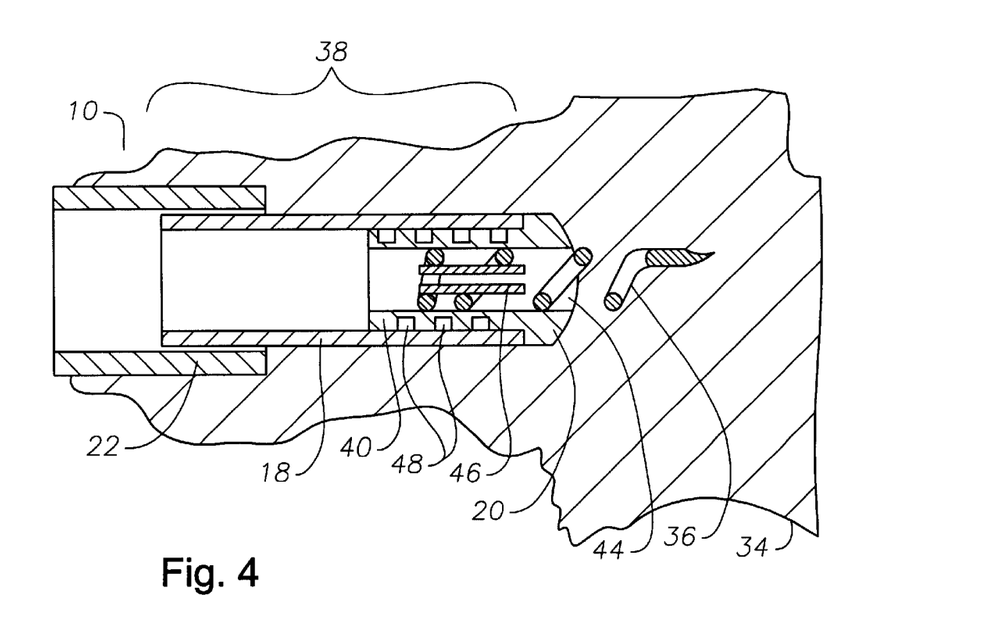
FIG. 4 is a cross-sectional view like FIG. 2 depicting the lead after disconnection and withdrawal of a segment of the lead in accordance with the present invention.

The segment 18 is coupled to the segment 14 by the jacket 22. The segments 14 and 18 and the jacket 22 collectively define a lumen 51. The jacket 22 functions as a breakaway structure to enable the segment 14 to be readily broken away from the segment 18 in the event the lead 10 must be removed. After the segment 14 is removed, only the segment 18 and the jacket 22 are left in situ. In this way, nearly the entire length of the lead 10 may be easily removed without the need for heavy pulling forces or the attendant risks of cutting fibrous tissue. To provide the desired breakaway functionality, the jacket 22 is fabricated as a cylindrical structure composed of a thermally-sensitive shape-memory polymeric material. The shape-memory quality of the polymeric material enables the jacket 22 to deform from a temporary shape to a permanent shape in response to thermal stimulation. In FIG. 2, the jacket 22 is depicted in a temporary shape with an inner diameter that is slightly smaller than the outer diameter of the segments 18 and 14 to establish an interference fit that securely holds the segments 18 and 14. The segment 18 may be further secured to the jacket 22 by a suitable medical grade adhesive, such as silicone, the two-part adhesive Polycin/Vorite supplied by CasChem, Inc., or similar adhesives. FIG. 3 shows the jacket 22 following thermal stimulation and deformation substantially back into the permanent shape. The permanent shape is such that the inner diameter of the jacket 22 is larger than the outer diameter of the segment 14, enabling the segment 14 to be readily withdrawn. FIG. 4 shows the remaining components following removal of the segment 14.

The principle may be applied in reverse. The jacket 22 may be provided with a permanent shape with a smaller diameter than the segments 14 and 18, inserted into the opposing ends of the segments 14 and 18 and expanded to a temporary shape that yields an interference fit. Subsequent heating will shrink the jacket 22 and release the segment 14.

The aforementioned heat-sensitive shape-memory polymer behaves generally like a rigid material while at temperatures below the glass transition temperature $T_g$, but undergoes significant softening and may be readily plastically deformed when heated above $T_g$. When the material is then cooled below $T_g$, the deformation is fixed and the shape remains stable. However, the original shape of the material may be recovered by reheating the material above $T_g$.

During production, the jacket 22 is first molded into the permanent shape shown in FIG. 3. A variety of well known molding techniques may be used to create the jacket 22, such as injection molding, extrusion molding, or like techniques. The molding process subjects the heat-sensitive shape-memory polymeric material to a temperature well in excess of the $T_g$ for the material for a sufficient time to form the jacket 22 into the permanent shape. Thereafter, the jacket 22 may be deformed into the temporary shape shown in FIG. 2 by deforming the jacket 22 at a temperature above $T_g$, and maintaining the jacket 22 in the temporary shape while the temperature is lowered below $T_g$. After cooling below $T_g$, the jacket 22 retains the temporary shape. However, if the jacket 22 is later heated above $T_g$, it will deform substantially back into the permanent shape in which it was originally molded. In this way, the jacket 22 may be initially produced with a permanent shape that will enable ready establishment of the requisite interference fit with the segments 14 and 18.

Where molding of the desired permanent shape is difficult in view of the molding process used and the small dimensions of the jacket 22, the jacket 22 may be molded with a first permanent shape that best suits the molding process. This may be, for example, a shape with a larger than desired permanent diameter. Thereafter, the jacket 22 may be provided with a new permanent shape by heating the jacket 22 above $T_g$, deforming the jacket 22 into a new desired permanent shape, (e.g. a shape with a more suitable permanent diameter) and maintaining the jacket 22 in that shape and at that temperature for a selected period of time. The heating time required to set the new permanent shape will depend on the particular polymer.

Referring again to FIGS. 3 and 4, removal of some or all of the conductor wire 50 should accompany complete removal of the segment 14. Whether some or all of the conductor wire 50 may be readily removed will depend on how the wire 50 is coupled to the tip electrode 20. In the embodiment illustrated in FIGS. 3 and 4, the conductor wire 50 will unwind from the proximal end 40 when the segment 14 is withdrawn. However, if the wire 50 does not freely unwind from the proximal end 40 or is otherwise secured to the tip electrode 20, it may be necessary to fracture the wire 50, remove the portion of the wire 50 coupled to the connector 16 (see FIG. 1) and leave the portion of the wire 50 secured to the tip electrode 20 in place. If fracture is necessary, it is advantageous for the fracture to occur so that little of the wire 50 remaining in situ projects from the jacket 22 following removal of the segment 14 and the portion of the wire 50 removed with the segment 14.

The wire 50 may be fractured by holding the segment in a fixed position and twisting the connector 16, which, in turn, twists the segment 14. The segment 18 will ordinarily be prevented from twisting by the fibrous tissue 38. However, since the conductor wire 50 is not directly attached to the segment 14, the mere twisting of the segment 14 will result in a torque being applied to the wire 50 near the connector 16 and not near the segment 18. As a result, the wire 50 may fracture somewhere inside the segment 14 and a significant portion of the wire 50 connected to the tip electrode 20 may be left in situ after the segment 14 is removed. To ensure that the wire 50 fractures near the segment 18, it is necessary to secure the wire 50 to the segment 14 very near the distal end of the segment 14. In this way, twisting of the segment 14 will result in a torque applied to the wire 50 at the point where the wire 50 and the segment 14 are coupled and a fracture of the wire 50 in the vicinity of the segment 18.

Figure 5:
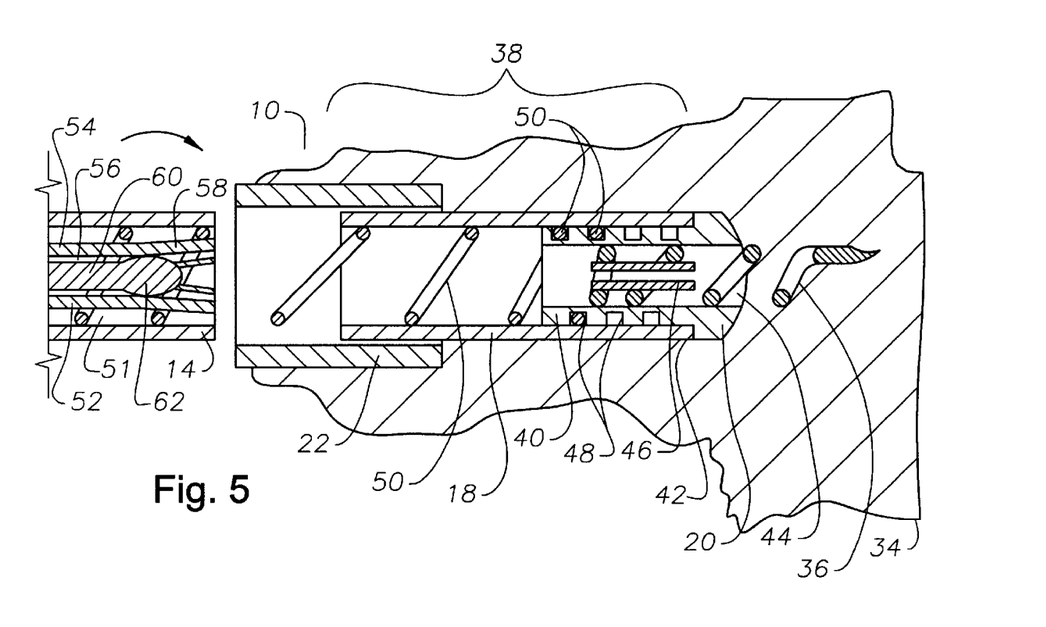
FIG. 5 is a cross-sectional view like FIG. 2 depicting insertion of a wire anchor into the lead in accordance with the present invention.

Referring now to FIG. 5, the wire 50 may be temporarily secured near the distal end of the segment 14 by a wire anchor 52 that may be inserted into the connector 16 (see FIG. 1) and advanced into the lumen 51 to the position shown. The wire anchor 52 includes a tubular housing 54 that defines a longitudinal lumen 56. The housing 54 terminates distally in a collet 58. A stylet 60 that has an enlarged tip 62 may be inserted into the lumen 56 and advanced as shown. When the tip 62 encounters the collet 58, the collet 58 expands and compresses the wire 50 against the inner surface of the segment 14. The collet 58 clamps the wire 50 to the inner surface of the segment 14. When the segment 14 and the wire anchor 52 are twisted in unison, the portion of the wire 50 within the segment 14 twists along with the segment 14 and torque is applied to the wire 50 at the points where the wire 50 is clamped. The arrangement produces a torsional failure of the wire 50 distal to the clamped area and near the segment 18. The housing 54 is advantageously composed of a biocompatible material such as stainless steel, polyurethane, or suitable materials of sufficient ductility to enable ready bending of the collet 58. The stylet 60 is advantageously composed of a variety of biocompatible materials, such as titanium, stainless steel, or like materials.

Figure 6:
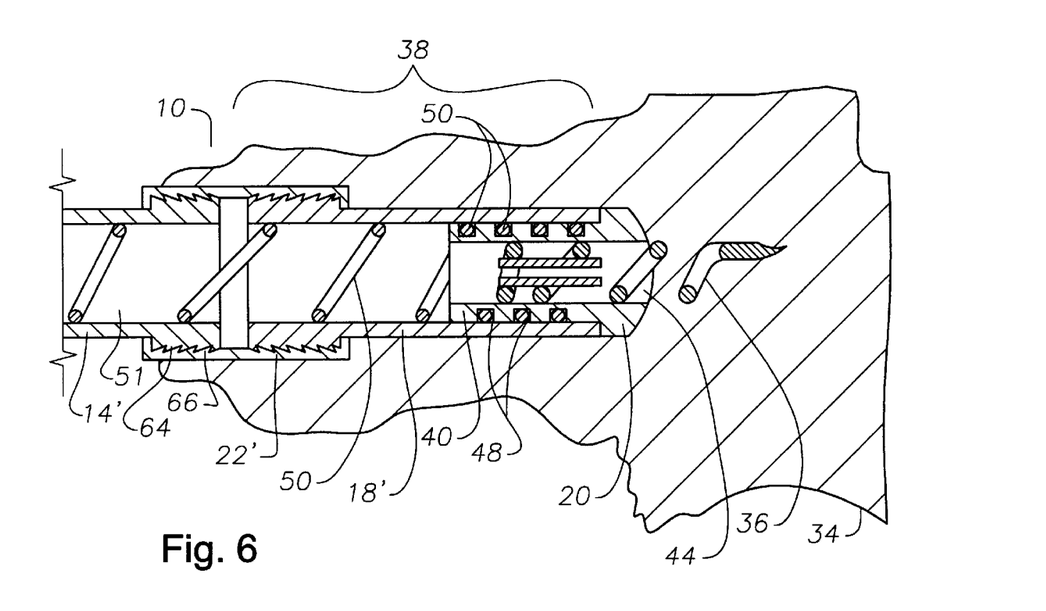
FIG. 6 is a cross-sectional view like FIG. 2 depicting an alternate embodiment of the segments and jacket of the lead of FIG. 1 in accordance with the present invention.

In an alternate embodiment depicted in FIG. 6, the interior surface of the jacket, now designated 22', and the exterior surfaces of the segments, now designated 14' and 18', may be provided, respectively, with cooperating ridges 64 and 66. The ridges 64 and 66 engage and inhibit axial movement of the segment 14' and 18" relative to the jacket 22' while the jacket 22' is in the temporary shape shown in FIG. 6. When the jacket 22' is expanded by thermal stimulation, the ridges 64 and 66 disengage, enabling removal of the segment 14'.

Figure 7:
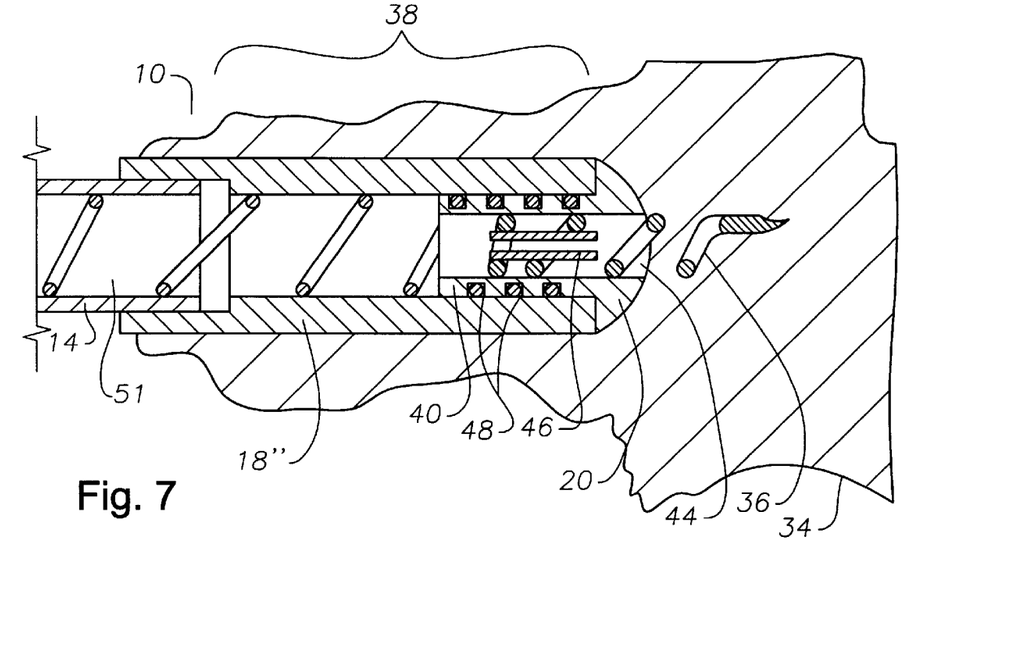
FIG. 7 is a cross-sectional view like FIG. 2 depicting another alternate embodiment of the lead without the jacket in accordance with the present invention.

In an alternate embodiment, the breakaway functionality may be incorporated directly into the segment 18. Referring now to FIG. 7, the segment, now designated 18", may be composed of a thermally-sensitive shape-memory polymeric material. FIG. 7 is a cross-sectional view from the same perspective as FIG. 2. The proximal end of the segment 18" is fabricated with a permanent shape having an inner diameter slightly larger than the outer diameter of the segment 14. Prior to implantation, the segment 14 is slipped inside the proximal end of the segment 18", and the segment 18" is heated above $T_g$ and deformed into a temporary shape with an inner diameter that is slightly smaller than the outer diameter of the segment 14 so that the segment 14 is secured to the segment 18" by interference. If it is necessary to disengage the segment 14 from the segment 18" following implantation, the segment 18" is heated above $T_g$ in situ. The segment 18" expands back substantially to the permanent shape, and the segment 14 is released. The same principle may be applied in reverse, that is, the segment 14 may be formed from a shape-memory polymeric material and deformed in situ to provide the breakaway functionality.

Figure 8:
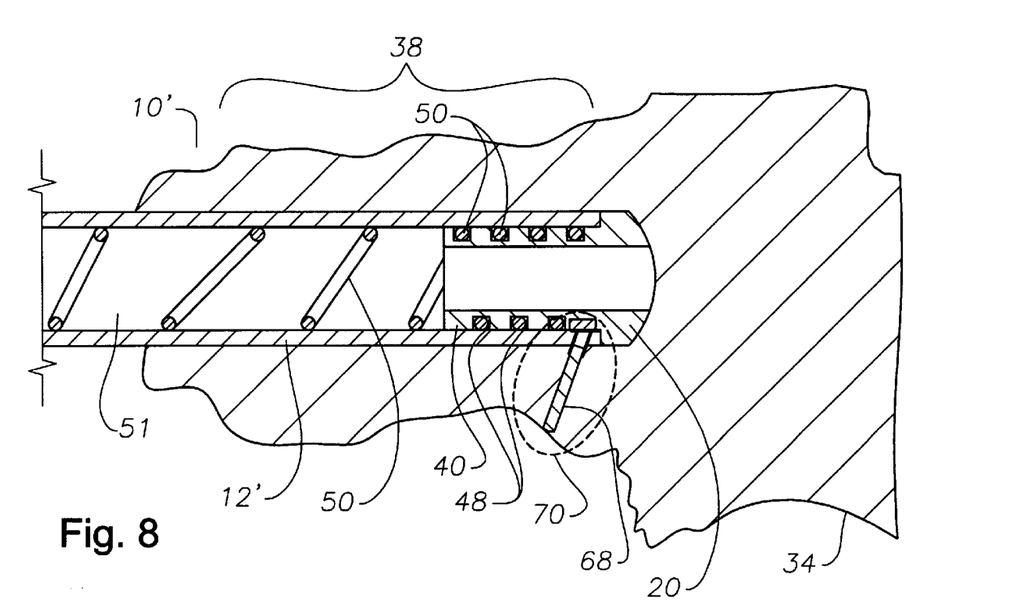
FIG. 8 is a cross-sectional view like FIG. 2 depicting an alternate embodiment of the lead of FIG. 1 incorporating a tine and tine clamp in accordance with the present invention.
Figure 9:
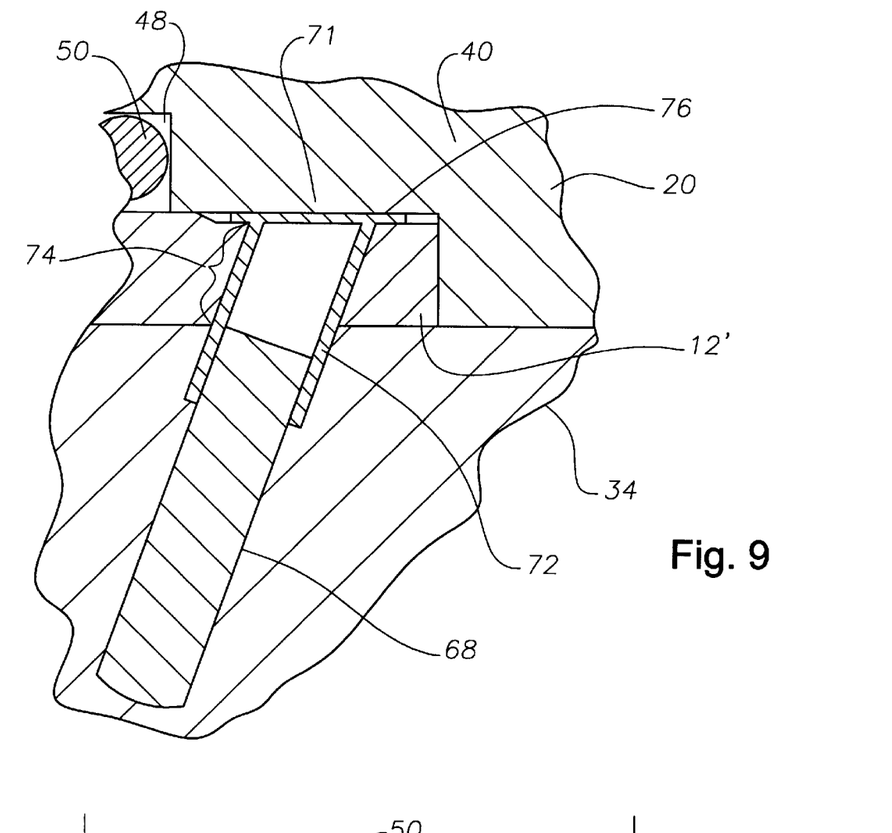
FIG. 9 is a detailed cross-sectional view of the tine depicted in FIG. 8 in accordance with the present invention.

In another alternate embodiment, the breakaway functionality may be applied to lead structures used for passive fixation. FIG. 8 is a cross-sectional view like FIG. 2 of a lead, now designated 10', incorporating passive fixation in the form of a radially projecting tine 68. There may be several tines 68. FIG. 9 is a detailed view of the portion of FIG. 8 identified by the dashed oval 70. The tine 68 is secured to the lead 10' by a clamp 71. The clamp 71 includes a cylindrical member 72 that projects through an opening 74 in the sleeve, now designated 12'. The upper end of the cylindrical member includes a base 76 that is sandwiched between the sleeve 12' and the exterior surface of the proximal end 40 of the tip electrode 20. The base 76 is wider than the diameter of the opening 74. During assembly, the cylindrical member 72 is inserted through the opening from inside the sleeve 12'. The base 74 prevents the cylindrical member 72 from popping out of the opening 74. The tine 68 is disposed in the lower end of the cylindrical member 72 and secured thereto by interference. The tine 68 may be composed of a variety of biocompatible materials, such as silicone, polyurethane, or like materials.

The clamp 71 is composed of a thermally-sensitive shape-memory polymeric material of the type described above. The clamp 71 is fabricated with a permanent shape such that the inner diameter of the cylindrical member 72 is slightly larger than the outer diameter of the tine 68. Prior to implantation, the tine 68 is inserted into the cylindrical member 72 and the cylindrical member 72 is deformed into the temporary shape shown in FIGS. 8 and 9 to hold the tine 68 via interference. If the lead 10' must be removed following implantation and development of the fibrous tissue 38, the clamp 71 may be heated above $T_g$ to deform the cylindrical member 72 to the permanent shape. The lead 10' may then be withdrawn, leaving only the tine 68 in situ. Heat may be transferred to the clamp 71 by flowing heated fluid through the sleeve 12' or by other methods described below.

Figure 10:
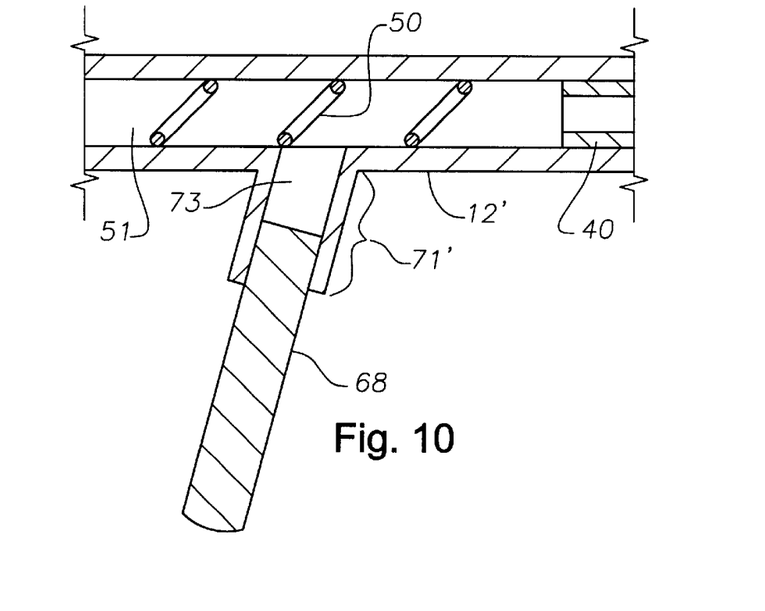
FIG. 10 is a view like FIG. 9 depicting an alternate embodiment of the tine clamp in accordance with the present invention.

In an alternate embodiment depicted in FIG. 10, the clamp, now designated 71', is integrally molded with the sleeve 12' and provided with a lumen 73 that is in fluid communication with the lumen 51 in the sleeve 12'. The lumen 73 enables heating fluid flowing in the lumen 51 to bathe and thermally stimulate the clamp 71'.

Figure 11:
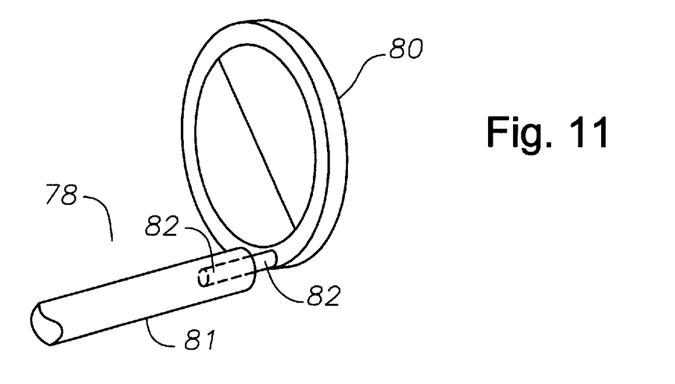
FIG. 11 is a pictorial view of an introducer assembly for manipulating a medical device in vivo in accordance with the present invention.
Figure 12:
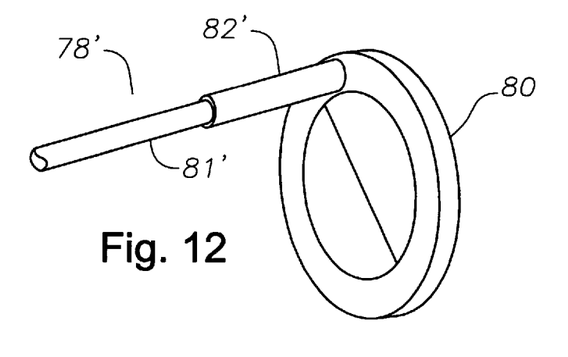
FIG. 12 is a pictorial view of an alternate embodiment of an introducer assembly for manipulating a medical device in vivo in accordance with the present invention.

The breakaway functionality may be applied to structures other than cardiac leads. FIGS. 11 and 12 depict pictorial views of introducer assemblies 78 and 78' for inserting an implantable medical device into the body. The illustrated medical device is an artificial heart valve 80, and for simplicity of illustration, the suture ring of the valve 80 is not shown. As shown in FIG. 11, the introducer assembly 78 includes an introducer 81 having a bore 82 for receiving a pin 84 that is coupled to the valve 80. The introducer 81 is composed of shape-memory polymeric material to provide the breakaway feature described in conjunction with the aforementioned embodiments. In the introducer assembly 78' shown in FIG. 12, the functions of the introducer, now designated 81', and the pin, now designated 82' are flip-flopped. The pin 82' includes a bore 86 for receiving the introducer 81'. As described above, when the pin 82' is stimulated in situ, the introducer 81' is released and may be removed from the body.

The materials selected for the deforming structures, such as the jacket 22, the segment 18", the clamp 71, or the introducers 81 or 81' should have glass transition temperatures that are above the anticipated maximum body temperature so that they do not soften and deform into undesirable shapes after implantation. Normal body temperature usually falls within the range 36 to 37° C. However, a body subjected to high fever may reach about 42° C., so a $T_g \geq 42°$ C. should ensure that the deforming structures do not undergo undesirable deformation after implantation.

For long-term implantation, the deforming structures, such as the jacket 22, the segment 18", the clamp 71, or the introducers 81 or 81' may be fabricated from heat-sensitive shape memory polymers such as polynorbornene supplied by Nippon Zeon of Japan, polyurethane supplied by Mitsubishi Heavy Industries of Japan, Calo.Mer™ supplied by Polymer Technology Group of California, or similar materials. If the lead 10 is designed for more transient implantation, materials such as polyvinyl chloride, or similar materials may be used in addition to the above-described materials. Metallic materials, such as, for example, Nitinol, or similar materials coated with biocompatible polymeric materials, such as polyurethane may also be used. It is desirable to heat the particular deforming structure in situ. This may be accomplished by introducing a heated fluid into the lumen 51 via the syringe 28 coupled to the adaptor 26 shown in FIG. 1. The lumen 44 in the tip electrode 20 permits the heated fluid to flow through the lumen 51 past the jacket 22 and out the lumen 44 into the body. The heated fluid should be a biocompatible, body absorbable fluid, such as, for example, saline, alcohol, or like fluids. Other heating methods may be employed as discussed below.

Figure 13:
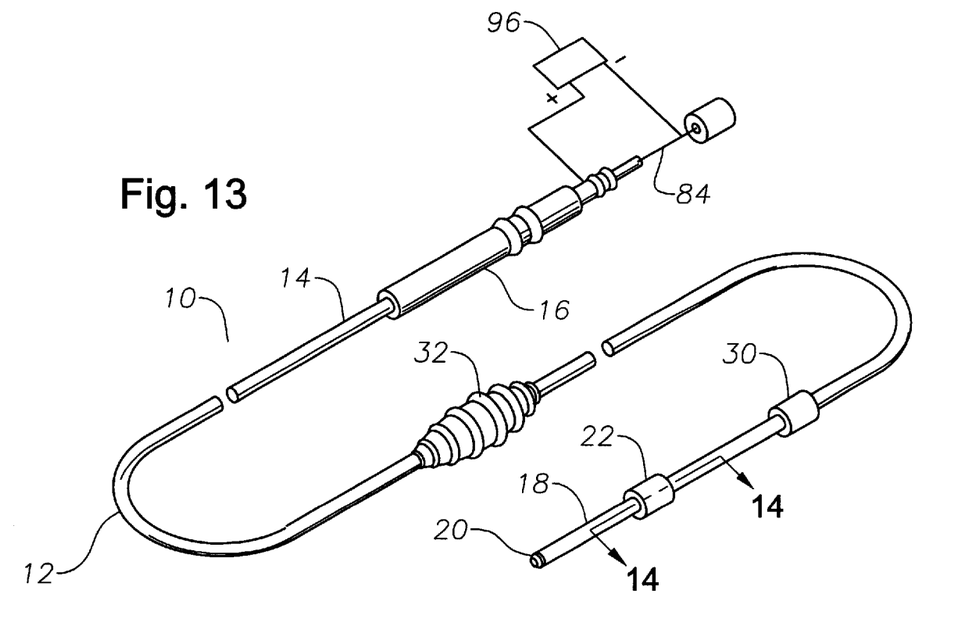
FIG. 13 is a pictorial view of the cardiac lead of FIG. 1 depicting insertion of a heated stylet and connection of a voltage source to the stylet in accordance with the present invention.
Figure 14:
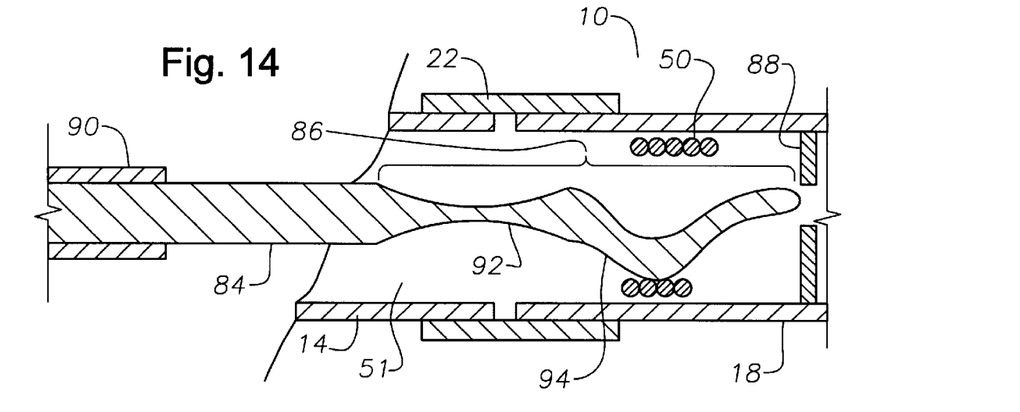
FIG. 14 is a cross-sectional view of FIG. 13 taken at section 14—14 in accordance with the present invention.
Figure 15:
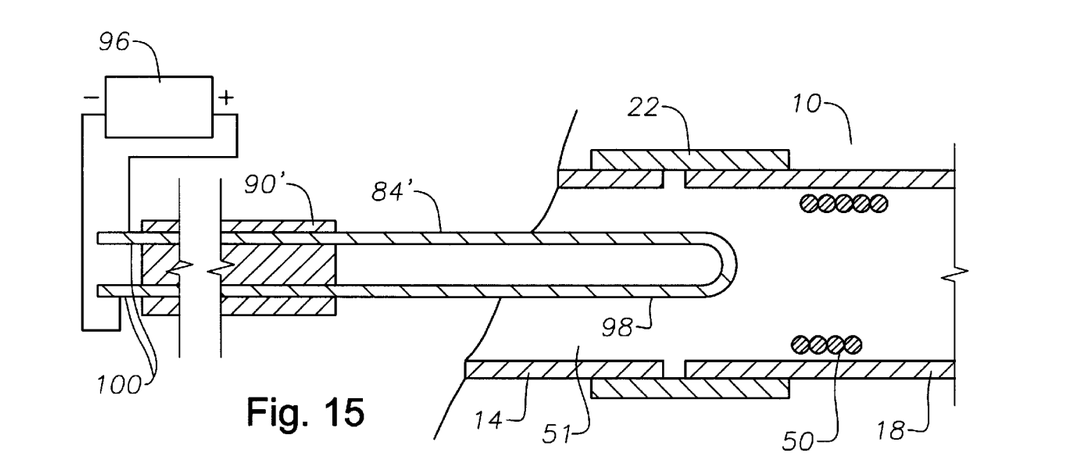
FIG. 15 is a cross-sectional view like FIG. 14 of an alternate embodiment of the stylet coupled to a voltage source in accordance with the present invention.

Alternatively, and as depicted in FIGS. 13, 14 and 15, heat may be transferred to the jacket 22 or other deformable structure by means of a heated stylet 84 that is introduced into the lumen 51. FIG. 13 depicts a pictorial view of an exemplary embodiment of the stylet 84 suitable for use with a lead 10 incorporating a conductor wire 50 that is not individually insulated. FIG. 14 is a cross-sectional view of FIG. 13 taken at section 14—14. The stylet 84 is advanced into the lumen 51 until the tip 86 of the heated stylet 84 is near the jacket 22. For the purpose of preventing the stylet tip 86 from moving substantially past the jacket 22, the segment 18 may be fitted with an annular member 88 positioned distal to the jacket 22. The stylet 84 is advantageously composed of an electrically conducting material, such as stainless steel, titanium, or similar suitable materials coated with an electrically insulating coating 90. The tip 86 is provided with a tapered portion 92 and an arcuate portion 94 not covered by the coating 90. The tapered portion 92 will more readily dissipate $I^2R$ losses in the form of heat when current is passed through the stylet 84 as a result of the diminished cross-sectional area. A voltage source 96 is coupled to the proximal end of the stylet 84 and the connector 16. The arcuate 94 portion of the stylet 84 contacts the conductor wire 50 to complete the circuit.

An alternative embodiment of the heated stylet, now designated 84', is shown in FIG. 15, which is a cross-sectional view similar to the view depicted in FIG. 14. The length of the stylet 84' is such that it is shown broken. This embodiment is suitable for transferring heat where the conductor wire 50 is separately insulated and cannot be used to complete a circuit with the voltage source 96. Here, the stylet 84' consists of a conducting wire bent into two parallel sections partially coated by the coating, now designated 90', so as to form a conducting loop 98 distally. The voltage source 96 is coupled across the proximal ends 100 of the stylet 84' to complete the circuit.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents and alternatives falling within the spirit and scope of the invention as defined by the following appended claims.

What is claimed is:

1. A cardiac lead, comprising:

a connector for coupling to a cardiac stimulator;

a flexible sleeve coupled to the connector and having a first lumen;

a clamp coupled to the flexible sleeve and being composed of a shape-memory polymeric material;

a tine coupled to the clamp and having an end projecting away from the flexible sleeve whereby the clamp may be selectively deformed diametrically in situ to disconnect the tine from the clamp;

an electrode coupled to the sleeve; and a conductor wire coupled to the connector and to the electrode for conveying electrical signals.

2. The cardiac lead of claim 1, comprising a second electrode coupled to the sleeve and a second conductor coupled to the second electrode and the connector.

3. The cardiac lead of claim 1, wherein the clamp has a second lumen in fluid communication with the first lumen to enable fluid to flow into the clamp.

4. The cardiac lead of claim 1, wherein the clamp comprises a cylindrical member, the tine being disposed in the cylindrical member, and the cylindrical member expands diametrically in situ.

* * * * *